United States Patent
Martinez et al.

(10) Patent No.: US 6,753,446 B1
(45) Date of Patent: Jun. 22, 2004

(54) SYNTHESIS OF LABELED OXALIC ACID DERIVATIVES

(75) Inventors: Rodolfo A. Martinez, Santa Fe, NM (US); Clifford J. Unkefer, Los Alamos, NM (US); Marc A. Alvarez, Santa Fe, NM (US)

(73) Assignee: The Regents of the University of California, Los Alamos, NM (US)

( * ) Notice: Subject to any disclaimer, the term of this patent is extended or adjusted under 35 U.S.C. 154(b) by 0 days.

(21) Appl. No.: 10/456,081

(22) Filed: Jun. 5, 2003

(51) Int. Cl.$^7$ .................. C07C 229/00; C07C 69/34; C07C 327/00
(52) U.S. Cl. .............. 560/155; 560/190; 558/255
(58) Field of Search .................. 560/155, 190; 558/255

(56) References Cited

PUBLICATIONS

Wilmes et al, Journal of Labeled Compounds and Radiopharmaceuticals, Preparation of Mono–15N–Cyanogen and Mono–13C–Cyanogen, 1992, 31(12), pp. 1037–1040.*

* cited by examiner

Primary Examiner—Michael L. Shippen
Assistant Examiner—Paul A. Zucker
(74) Attorney, Agent, or Firm—Bruce H. Cottrell

(57) ABSTRACT

The present invention is directed to labeled compounds, specifically

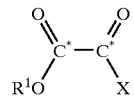

where each C* is selected from the group consisting of a carbon-12, i.e., $^{12}C$, or a carbon-13, i.e., $^{13}C$ and at least one C* is $^{13}C$, $R^1$ is selected from the group of $C_1$–$C_4$ lower alkyl and aryl, and X is selected from the group of —$NR^2R^3$ where $R^2$ and $R^3$ are each independently selected from the group of $C_1$–$C_4$ lower alkyl, alkoxy and aryl, —$SR^4$ where $R^4$ is selected from the group of $C_1$–$C_4$ lower alkyl, alkoxy and aryl, and —$OR^5$ where $R^5$ is selected from the group of $C_1$–$C_4$ lower alkyl, alkoxy and aryl with the proviso that when $R^1$ is methyl then $R^5$ is other than methyl, when $R^1$ is ethyl then $R^5$ is other than ethyl, and when $R^1$ is benzyl then $R^5$ is other than benzyl.

5 Claims, No Drawings

SYNTHESIS OF LABELED OXALIC ACID DERIVATIVES

STATEMENT REGARDING FEDERAL RIGHTS

This invention was made with government support under Contract No. W-7405-ENG-36 awarded by the U.S. Department of Energy. The government has certain rights in the invention.

FIELD OF THE INVENTION

The present invention relates to labeled compounds and more particularly to isotopically enriched acetic acid, (dialkylamino)oxo-, alkyl esters labeled with carbon-13 or with carbon-13 and hydrogen-2.

BACKGROUND OF THE INVENTION

Diethyloxalate is an extremely useful synthon for the synthesis of many important biochemicals and pharmaceuticals. It can be used as a labeling synthon but has limitations in that it can only be used as a symetrically labeled compound. A new synthon has now been developed that has the synthetic utility of diethyl oxalate and allows the differentiation of each of the carbons.

It is an object of the present invention to provide labeled compounds useful for synthetic chemistry development.

SUMMARY OF THE INVENTION

In accordance with the purposes of the present invention, as embodied and broadly described herein, the present invention provides labeled compounds of the formula

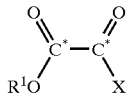

where each C* is selected from the group consisting of a carbon-12, i.e., $^{12}C$, or a carbon-13, i.e., $^{13}C$ and at least one C* is $^{13}C$, $R^1$ is selected from the group of $C_1$–$C_4$ lower alkyl and aryl, and X is selected from the group of —$NR^2R^3$ where $R^2$ and $R^3$ are each independently selected from the group of $C_1$–$C_4$ lower alkyl, alkoxy and aryl, —$SR^4$ where $R^4$ is selected from the group of $C_1$–$C_4$ lower alkyl, alkoxy and aryl, and —$OR^5$ where $R^5$ is selected from the group of $C_1$–$C_4$ lower alkyl, alkoxy and aryl with the proviso that when $R^1$ is methyl then $R^5$ is other than methyl, when $R^1$ is ethyl then $R^5$ is other than ethyl, and when $R^1$ is benzyl then $R^5$ is other than benzyl. In specific embodiments, the labeled compounds include [1-$^{13}C$]acetic acid, (dimethylamino)oxo-, ethyl ester, [2-$^{13}C$]acetic acid, (dimethylamino)oxo-, ethyl ester, and [1,2-$^{13}C_2$]acetic acid, (dimethylamino)oxo-, ethyl ester.

DETAILED DESCRIPTION

The present invention is concerned with diethyl oxalate analogs useful for assymetric labeling of synthetic compounds. Generally, the compounds are labeled with carbon-13, although they may be labeled with deuterium ($^2H$) as well.

Particularly, the present invention is concerned with labeled compounds of the formula

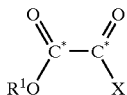

where each C* is selected from the group consisting of a carbon-12, i.e., $^{12}C$, or a carbon-13, i.e., $^{13}C$ and at least one C* is $^{13}C$, $R^1$ is selected from the group of $C_1$–$C_4$ lower alkyl and aryl, and X is selected from the group of —$NR^2R^3$ where $R^2$ and $R^3$ are each independently selected from the group of $C_1$–$C_4$ lower alkyl, alkoxy and aryl, —$SR^4$ where $R^4$ is selected from the group of $C_1$–$C_4$ lower alkyl, alkoxy and aryl, and —$OR^5$ where $R^5$ is selected from the group of $C_1$–$C_4$ lower alkyl, alkoxy and aryl with the proviso that when $R^1$ is methyl then $R^5$ is other than methyl, when $R^1$ is ethyl then $R^5$ is other than ethyl, and when $R^1$ is benzyl then $R^5$ is other than benzyl.

As used herein, the term "lower alkyl" refers to $C_1$–$C_4$ alkyl such as methyl, ethyl, n-propyl, iso-propyl, butyl, isobutyl, and tert-butyl while the term "aryl" means a monovalent monocyclic or bicyclic aromatic hydrocarbon radical of 6 to 10 ring atoms, and optionally substituted independently with one, two, three, four or five substituents selected from alkyl, haloalkyl, cycloalkyl, halo, nitro, cyano, —OR (where R is hydrogen, alkyl, haloalkyl, cycloalkyl, optionally substituted phenyl), acyl, and —COOR (where R is hydrogen or alkyl). More specifically, the term "aryl" includes, but is not limited to 1-naphthyl, substituted 1-naphthyl, 2-naphthyl, substituted 2-naphthyl, and phenyl groups with the structure

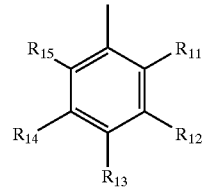

wherein $R_{11}$, $R_{12}$, $R_{13}$, $R_{14}$ and $R_{15}$ are each independently a lower alkyl, i.e., a $C_1$–$C_4$ alkyl such as methyl, ethyl, n-propyl, iso-propyl, butyl, isobutyl, and tert-butyl, a halogen such as chloro, bromo or iodo, an amino group such as $NH_2$, NHR or NRR' where R and R' are each a lower alkyl or aryl as described above, or an alkoxy group such as O-alkyl or O-aryl where the alkyl is a lower alkyl as described above or an aryl as described above. Additionally, the aryl group may be a benzyl group.

Among particular labeled compounds are included [1-$^{13}C$]acetic acid, (dimethylamino)oxo-, ethyl ester, [2-$^{13}C$]acetic acid, (dimethylamino)oxo-, ethyl ester, and [1,2-$^{13}C_2$]acetic acid, (dimethylamino)oxo-, ethyl ester.

Each of these labeled compounds can be synthesized from similar starting materials, e.g., methyl phenyl sulfide.

In an exemplary process of the present invention, C*$O_2$ where C* is $^{12}C$ or $^{13}C$ is reacted with a [$^{12}C$ or $^{13}C$]methyl phenyl sulfide to form an addition product, a chlorination reaction is conducted with the addition product to form an acid chloride-containing intermediate, an exchange reaction is conducted between dimethyl amine and the acid chloride-containing intermediate, and reaction with thionyl chloride is conducted followed by reaction with an ethanol-water mixture to yield the labeled compound.

Unlike labeled diethyl oxalate, the reactivity of the labeled acetic acid, (dimethylamino)oxo-, ethyl esters can be tailored to produce a variety of labeled biochemicals and pharmaceuticals with predictable regioselectivity. For example, a general reaction for the production of isotopically labeled glycerol using such a reagent can be as follows.

Lithium methyl phenyl sulfide can be reacted with any one of the described labeled acetic acid, (dimethylamino) oxo-, ethyl esters in THF to form an intermediate product. Such an intermediate product can then be reacted with diisobutylaluminum hydride (DIBAL) followed by reaction with acetic anhydride and sodium acetate and followed by reaction with lithium borohydrate to form differently labeled glycerols. In the case of [1-$^{13}$C]acetic acid, (dimethylamino) oxo-, ethyl ester as a starting material, the product will be [1,3-$^{13}$C$_2$]glycerol. In the case of [2-$^{13}$C]acetic acid, (dimethylamino)oxo-, ethyl ester as a starting material, the product will be [1,2-$^{13}$C$_2$]glycerol. In the case of [1,2-$^{13}$C$_2$] acetic acid, (dimethylamino)oxo-, ethyl ester as a starting material, the product will be [U-$^{13}$C$_3$]glycerol.

The present invention is more particularly described in the following examples which are intended as illustrative only, since numerous modifications and variations will be apparent to those skilled in the art.

EXAMPLE 1

Preparation of [1-$^{13}$C]acetic acid, (dimethylamino)oxo-, ethyl ester was as follows. [$^{13}$C]Methyl phenyl sulfide was reacted with sec-butyl lithium followed by [$^{13}$C]carbon dioxide to form intermediate (I). This intermediate (I) was then reacted with oxalyl chloride followed by dimethyl amine to form intermediate (II). This intermediate (II) was then reacted with sulfuryl chloride followed by 10 percent water in ethanol to form [1-$^{13}$C]acetic acid, (dimethylamino) oxo-, ethyl ester.

EXAMPLE 2

Preparation of [2-$^{13}$C]acetic acid, (dimethylamino)oxo-, ethyl ester was as follows. [$^{13}$C]Methyl phenyl sulfide was reacted with sec-butyl lithium followed by carbon dioxide to form intermediate (III). This intermediate (III) was then reacted with oxalyl chloride followed by dimethyl amine to form intermediate (IV). This intermediate (IV) was then reacted with sulfuryl chloride followed by 10 percent water in ethanol to form [2-$^{13}$C]acetic acid, (dimethylamino)oxo-, ethyl ester.

EXAMPLE 3

Preparation of [1,2-$^{13}$C$_2$]acetic acid, (dimethylamino) oxo-, ethyl ester was as follows. Methyl phenyl sulfide was reacted with sec-butyl lithium followed by [$^{13}$C]carbon dioxide to form intermediate (V). This intermediate (V) was then reacted with oxalyl chloride followed by dimethyl amine to form intermediate (VI). This intermediate (VI) was then reacted with sulfuryl chloride followed by 10 percent water in ethanol to form [1,2-$^{13}$C$_2$]acetic acid, (dimethylamino)oxo-, ethyl ester.

Although the present invention has been described with reference to specific details, it is not intended that such details should be regarded as limitations upon the scope of the invention, except as and to the extent that they are included in the accompanying claims.

What is claimed is:

1. A labeled compound of the formula

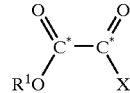

where C* is selected from the group consisting of $^{12}$C and $^{13}$C and at least one C* is $^{13}$C, R$^1$ is selected from the group of C$_1$–C$_4$ lower alkyl and aryl, and X is selected from the group of —NR$^2$R$^3$ where R$^2$ and R$^3$ are each independently selected from the group of C$_1$–C$_4$ lower alkyl, alkoxy and aryl, —SR$^4$ where R$^4$ is selected from the group of C$_1$–C$_4$ lower alkyl, alkoxy and aryl, and —OR$^5$ where R$^5$ is selected from the group of C$_1$–C$_4$ lower alkyl, alkoxy and aryl with the proviso that when R$^1$ is methyl then R$^5$ is other than methyl, when R$^1$ is ethyl then R$^5$ is other than ethyl, and when R$^1$ is benzyl then R$^5$ is other than benzyl.

2. The labeled compound of claim 1 wherein X is selected from the group of —NR$^2$R$^3$ where R$^2$ and R$^3$ are each independently selected from the group of C$_1$–C$_4$ lower alkyl, alkoxy and aryl.

3. The labeled compound of claim 2 wherein said compound is [1-$^{13}$C]acetic acid, (dimethylamino)oxo-, ethyl ester.

4. The labeled compound of claim 2 wherein said compound is [2-$^{13}$C]acetic acid, (dimethylamino)oxo-, ethyl ester.

5. The labeled compound of claim 2 wherein said compound is [1,2-$^{13}$C$_2$]acetic acid, (dimethylamino)oxo-, ethyl ester.

* * * * *